United States Patent [19]

Randolph et al.

[11] 4,025,307
[45] May 24, 1977

[54] METHOD AND APPARATUS FOR DETERMINING CRYSTALLIZATION PROPERTIES OF URINE

[75] Inventors: Alan Randolph; George Drach; John Daniel Miller, all of Tucson, Ariz.

[73] Assignee: University Patents, Inc., Stamford, Conn.

[22] Filed: Jan. 23, 1976

[21] Appl. No.: 651,858

[52] U.S. Cl. .......................... 23/230 B; 23/253 R; 324/71 CP
[51] Int. Cl.$^2$ ................. G01N 15/06; G01N 21/22; G01N 33/16
[58] Field of Search ............. 23/230 B, 253 R, 259

[56] References Cited
OTHER PUBLICATIONS

Chemical Abstracts I, 69: 70908(a) (1968).
Chemical Abstracts II, 81: 83050n (1974).
Chemical Abstracts III, 82: 29413r (1975).

Primary Examiner—Morris O. Wolk
Assistant Examiner—Sidney Marantz
Attorney, Agent, or Firm—Martin Novack

[57] ABSTRACT

A method and apparatus for determining crystallization properties, such as the particle kinetics, of urine. A first feed solution is formulated as including synthetic urine plus an aliquot of natural urine. A second feed solution which includes synthetic urine is also formulated. The two feed solutions are combined in a continuous crystallizer and the particle densities or crystal populations of the contents of the crystallizer are measured. Finally, the particle kinetics, such as the nucleation and growth rate of the crystals, are calculated as a function of the measured particle densities. In the preferred embodiment, the first and second feed solutions each comprise synthetic urine plus an aliquot of natural urine, with the natural urine preferably having a concentration in the range of about three percent to thirty percent of the total. In this manner, the artificial urine is found to contribute the necessary stability and controls so that crystallization properties can be measured without undue "background" reactions yet enough natural urine is present to yield sufficient quantities of the constituents being measured to provide adequate sensitivity. Also, in the preferred embodiment of the invention, the two feed solutions respectively contain calcium and oxalate ions in amounts sufficient to cause supersaturation in the continuous crystallizer and contain components of the type necessary to obtain weddelite-type crystals of calcium oxalate in the dihydrate form.

20 Claims, 3 Drawing Figures

G = .324 microns/min.
B° = 35,000 nuclei/ml.-min.

METHOD AND APPARATUS FOR DETERMINING CRYSTALLIZATION PROPERTIES OF URINE

BACKGROUND OF THE INVENTION

This invention relates to techniques for analyzing body fluids and, more particularly, to a method and apparatus for determining crystallization of properties of urine.

The mechanisms of renal stone formation are not fully understood. This is particularly true of calcium oxalate and calcium phosphate stones which are quite common. Some investigators have offered evidence in support of the theory that the dominating cause of calcium oxalate stone formation is supersaturation of urine with calcium ions and oxalate ions. These investigators have generally set forth ex-vivo evidence in support of this "supersaturation" theory, but the causes of chemical changes which lead to the stone formation are not fully explained. It would appear that if supersaturation of urine alone causes renal calculi, correction of this cause by limitation of ion excretion might be readily achievable. However, treatment to reduce supersaturation of crystallizable ions has not been found completely successful in arrestng stone disease.

Other investigators have found evidence to support the theory that normal urine contains substances that inhibit the nucleation and/or growth of, or effect the solubility of, calcium oxalate. There have been certain indications, again not fully explained, that certain inhibiting substances found in normal urine are absent from the urine of stone formers.

It has been demonstrated that the particle size distribution of calcium oxalate crystals in fresh urine from recurrent stone formers is quite different than the distribution found in "control" non-stone-formers under the same conditions of dietary and fluid intake. For example, in an article entitled "Calcium Oxalate Crystalluria and Inhibitors of Crystallization in Recurrent Renal Stone-formers", which appeared in Volume 43 of "Clinical Science", it was reported that the crystals excreted by the controls were small and belong to a unimodal distribution, whereas those excreted by the stone-formers belong to a distribution which contained a second peak of much larger particles. In the same article, it was suggested that the urines of the controls contained an inhibitor of the growth and aggregation of calcium oxalate crystals in vitro and that the inhibitor was deficient in the urines of the recurrent stone-formers. While these findings are useful, it is necessary to enhance available data with information regarding the mechanisms of crystal growth and to measure the effects of the chemicals thought to be effective inhibitors, such as to determine the effectiveness of various treatments in producing the desired inhibiting action.

In an article entitled "The Inhibitory Effect of Urine on Calcium Oxalate Precipitation", which appeared in Volume 12, No. 6 of "Investigative Urology", there was described experiments in which a solution of natural urine in a buffered mixture containing calcium ions and oxalate ions had a measurable inhibitory effect on the formation of calcium oxalate precipitate. In these experiments the precipitate was recovered using a filter and calcium content was measured using flame photometry. In an attempt to determine the extent of inhibition of precipitation caused by the natural urine due to those urinary constituents known to affect calcium oxalate solubility, an "artificial urine", consisting of a mixture of nine salts and urea, was substituted for the natural urine and the experiments were repeated. In both cases (natural as well as artificial urine), it was found that the degree of inhibition of precipitate formation was related to the concentration of the urine in the solution. The "artificial urine" was found to have some inhibitory effect, but less than that of the same amount of natural urine.

The described prior art techniques, while useful, are limited by practical problems which arise in the attempt to isolate and determine the precise nature of the crystal forming and/or inhibiting effect of constituents in highly complicated natural urine. On the one hand, it would appear desirable to utilize relatively high concentrations of natural urine in performing experiments, since this apparently amplifies the effect to be measured and renders observations easier. On the other hand, due to the complex, variable, and still somewhat unknown nature of the constituents of natural urine and the reactions which occur in natural urine, the experimenter using relatively higher concentrations thereof must be concerned with "background reactions" which may tend to disturb measurements being taken by introducing unkown factors. A further practical limiting factor is that the amount of fresh natural urine from a particular subject being studied is limited by the subject's output, typically less than 2,000 milliliters per dayunder normal fluid intake conditions. Thus, techniques which require relatively large volumes of urine or numerous experiments to be performed using the urine of a given subject (each requiring a volume of urine) are rendered impractical.

In an article entitled "The Concept of a Continuous Crystallizer — Its Theory and Application to In Vivo and In Vitro Urinary Tract Models", by B. Finlayson, which appeared in Volume 9, No. 4 of "Investigative Urology", there is described an attempt at employing a "continuous crystallizer" for experiments wherein feed solutions including urine plus calcium and oxalate ions were crystallized under steady state conditions to determine properties of the crystallization process. The article cites a series of prior publications by Randolph et al which disclose various chemical engineering applications of particle balance to continuous crystallizers. In the Finlayson article, a "continuous crystallizer" is defined as any chamber continuously receiving a stream of supersaturated liquid and continuously ejecting a stream of liquid plus suspended particles. Finlayson reported employing a 550 milliliter continuous crystallizer into which were dripped the urine plus the salts including calcium and oxalate ions. After a number of system cycles had elapsed (i.e., cycles of mixing and removing to achieve a "steady state" of crystallization), measurements were taken on the reaction chamber contents by filtering to obtain the crystals and then making photomicrographs.

In addition to requiring a relatively large amount of urine, the Finlayson experiments apparently resulted in the precipitation of calcium oxalate monohydrate (whewellite-type) crystals. It is recognized that the mechanisms of stone formation in human urine generally involve the formation of dihydrate weddelite-type crystalline forms, but, to applicants' knowledge, these types of crystals are not generally obtainable using techniques which could be considered practical for analyzing patients under clinical conditions. Indeed, to aplicants' knowledge, there is no presently available clinical instrument which can measure, with a reasonable degree of confidence, the parameters of a particular patient's stone-forming propensity, or, for example, the high risk periods of a known stone-former.

It is an object of the invention to provide solution to the prior art problems as set forth and devise a method and apparatus of determining crystallization properties of urine which are both effective and practical. It is a further object of the invention to provide a type of equipment which can be employed clinically to determine, on a practical basis, the crystallization properties of urine from individual patients.

SUMMARY OF THE INVENTION

The present invention is directed to a method and apparatus for determining crystallization properties, such as the particle kinetics, of urine. In accordance with the method of the invention, a first feed solution is formulated as including synthetic urine plus an aliquot of natural urine. A second feed solution which includes synthetic urine is also formulated. The two feed solutions are combined in a continuous crystallizer and the particle densities or cyrstal populations of the contents of the crystallizer are measure. Finally, the particle kinetics, such as the nucleation and growth rate of the crystals, are calculated as a function of the measured particle densities.

In the preferred embodiment of the invented method, the first and second feed solutions each comprises synthetic urine with the total aliquot of natural urine (added to one or both feeds) preferably having a concentration in the range of about 3 percent to 30 percent of the total volume. In this manner, the artificial urine is found to contribute the necessary stability and controls so that crystallization properties can be measured without undue "background" reactions, yet enough natural urine is present to yield sufficient quantities of the constituents being measured to provide adequate sensitivity. Also, in the preferred embodiment of the invention, the two feed solutions respectively contain calcium and oxalate ions in amounts sufficient to cause supersaturation in the continuous crystallizer and contain components of the type necessary to obtain weddelite-type crystals of calcium oxalate in the dihydrate form. The effect of stone-inhibiting drugs can be evaluated with the present method by including appropriate concentrations of such drugs to one or both of the feed streams.

An apparatus in accordance with an embodiment of the invention comprises first and second feed receptacles for the urine-containing solutions. A mixed suspension mixed product removal crystallizer chamber is coupled to the first and second feed receptacles, preferably by continuous flow feed pumps. A particle counting means is adapted to receive samples of the chamber contents. Finally, a computer means, responsive to the output of the particle counting means, is provided for determining crystallization kinetics occurring in the chamber.

In the preferred embodiment of the apparatus, the volume of the chamber is of the order of 100 milliliters, and it is found that this unusually small volume does not interfere with the obtainment of proper steady state continuous crystallization, and the relatively accurate measurement of crystallization kinetics. In this embodiment, the flow rates are selected to give a substantially constant average residence time in the crystallizer chamber of about five to fifty minutes.

Further features and advantages of the invention will become more readily apparent from the following detailed description when taken in conjunction with the accompanying drawings.

BRIEF DESCRIPTON OF THE DRAWINGS

DESCRIPTION OF THE PREFERRED EMBODIMENT

Figure 1:
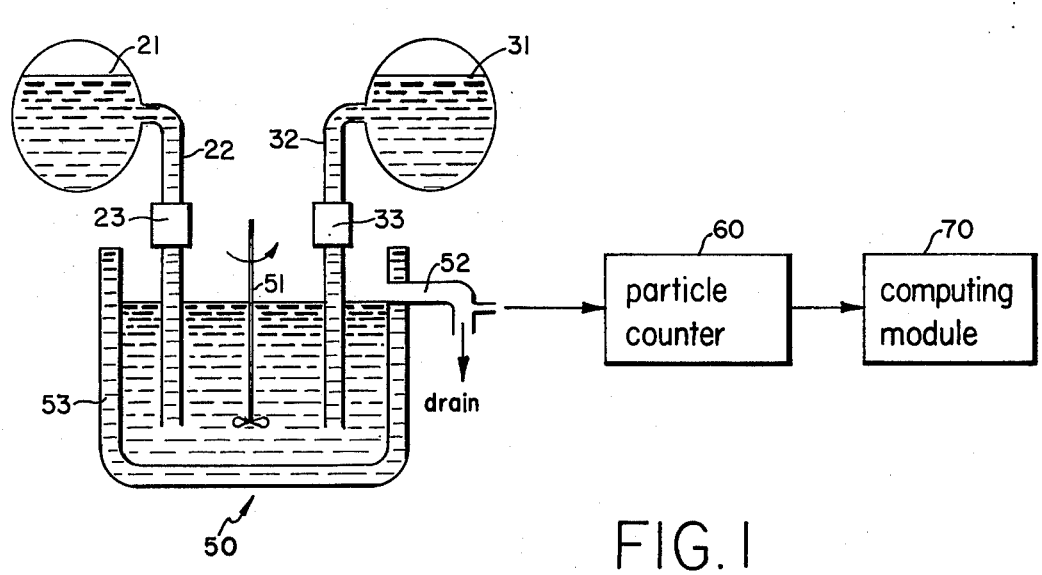
FIG. 1 is a schematic diagram which illustrates an apparatus in accordance with the present invention.

Referring to FIG. 1, there is shown a schematic representation, partially in block form, of an apparatus in accordance with an embodiment of the invention and which is useful in performing a method in accordance with the invention. First and second feed receptables 21 and 31 are provided to contain feed solutions to be described. These receptacles are respectively coupled, via tube 22 and continuous feed pump 23, and via tube 32 and continuous feed pump 33, to a continuous crystallizer 50. The pumps are preferably of the variable speed peristaltic type so that smooth non-pulsating flow is obtained. A single pump unit may be shared, if desired. In the present embodiment, the continuous crystallizer 50 is a continuous mixed suspension mixed product removal crystallizer of the general type described in an article entitled "Size Distribution Analysis in Continuous Crystallization" which appeared in "Chemical Engineering Progress Series" Volume 65, No. 95. In particular, the chamber 50 is continuously well stirred by a stirring rod 51 (powered by means not shown, and the amount of mixed product in the receptacle is maintained constant by the drain 52 and the continuous feed pumps 23 and 33 which provide a constant flow of non-particulate feed solution to the chamber. In the present embodiment, however, the volume of the chamber 50 is of substantially smaller volume than prior systems and has a capacity of the order of 100 milliliters. Also, the chamber 50 is maintained at a constant temperature of 38 ° C which simulates human body temperature, this being achieved by a constant temperature jacket 53 which continually receives recirculated fluid (by means not shown) from a constant temperature bath (not shown).

The output of the chamber 50 is sampled by a particle counting probe of a particle counter 60, which may typically be of the type manufactured by Particle Data, Inc., for example their Model No. 112 CLTSBN/ADC. The particle counter 60 generates an output which is a measure of the crystal populations of the steady state contents of the chamber 50. This information is coupled to a computing module 70 which calculates the crystallization properties (i.e., particle kinetics) of the contents of the chamber 50 as a function of the crystal populations.

In accordance with the preferred embodiment of the invention, the feed solution is feed receptacle 21 comprises synthetic urine plus an aliquot of natural urine and the feed solution in feed receptacle 31 comprises synthetic urine. One of the feed solutions, for example the one in feed receptacle 21, contains calcium ions, such as from calcium chloride added thereto, and the other feed receptacle contains oxatlate ions, such as from sodium oxalate added thereto. The concentration of calcium and oxalate ions is provided in amounts sufficient to cause supersaturation in the continuous crystallizer. As defined herein, the term "synthetic urine" is intended to mean a urine-like solution containing components of the type necessary to obtain weddelite-type crystals of calcium oxalate in the continuous crystallizer. In particular, the synthetic urine comprises a plurality of salts dissolved in water to obtain the cations sodium, potassium, calcium, ammonium and magnesium, and the anions chloride, sulfate, oxalate and phosphate.

Figure 2:
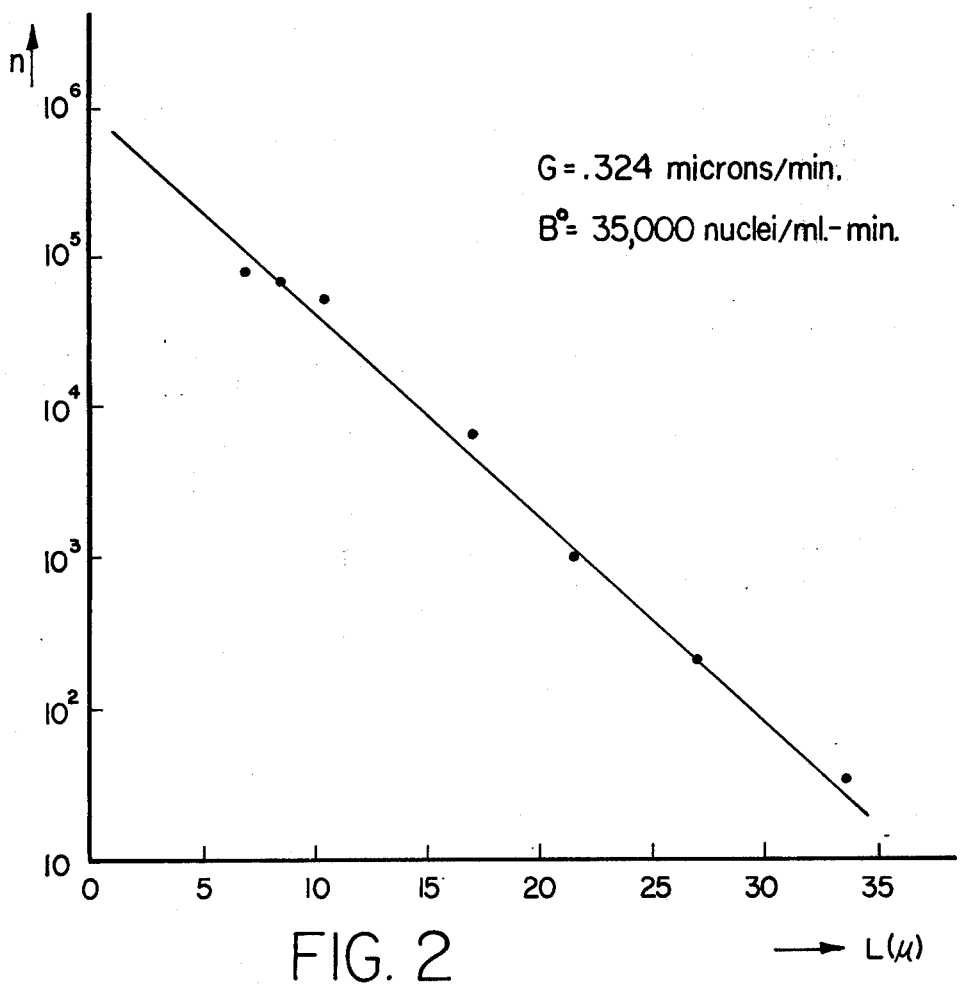
FIG. 2 is an experimental data plot useful in describing the invention.

It has been shown (e.g. by Larson and Randolph in an article entitled "Size Distribution Analysis in Continuous Crystallization", which appeared in Chemical Engineering Progress Symposium Series, Vol. 65, No. 95) that the population density of crystals propagated from supersaturation in a continuous mixed suspension mixed product removal crystallizer can be represented by the relationship $$n = (B^\circ/G) \exp(-L/GT)$$

where $n$ is the population density, $B^\circ$ is the nucleaton rate, $L$ is the crystal size, $G$ is the linear particle growth rate and $T$ is the "draw-down time" which is defined as the volume of the suspension divided by the volumetric feed and discharge rate. Accordingly by plotting the log of the populaton density as function of crystal size, the growth rate, $G$, can be determined from the slope of the line (which is $-1/GT$) and the intercept with the $n$ axis is determinative of the nucleation rate $B^\circ = n^\circ G$. FIG. 2, which is data from the EXAMPLES, is illustrative of the obtained plot.

Figure 3:
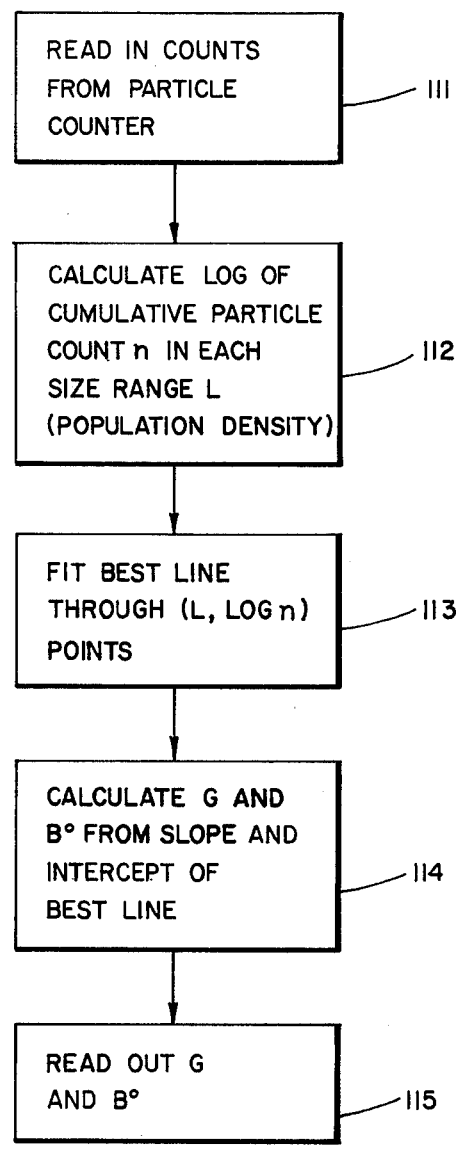
FIG. 3 is a simplified block diagram of the manner in which the general purpose computer can be programmed to achieve the functions of the computing module of FIG. 1.

FIG. 3 describes the programming of a general purpose digital computer, for example a minicomputer, or a special purpose dedicated minicomputer to perform the functions indicated by block 70 of FIG. 1. The particle size counts are read from the particle counter 60, as represented by block 111, and the log of the cumulative particle count, $n$, in each size range L, is calculated (block 112). A correlation routine is then employed to fit a "best line" through the points (L, log $n$), as represented by the block 113. The crystal growth rate, $G$, and the nucleation rate $B^\circ = n^\circ G$, are then calculated from the slope and intercept of the "best line" (block 114) and these values are read out, as represented by block 115.

EXAMPLE I

The following feed solutions were formulated in water:

| | Feed 1 | | Feed 2 |
|---|---|---|---|
| $Na_2SO_4$ | - 3.33 g/lit. | $Na_2SO_4$ | - 3.33 g/lit. |
| $NH_4Cl$ | - 3.18 | $NH_4Cl$ | - 3.18 |
| KCl | - 8.31 | KCl | - 8.31 |
| $MgSO_4 \cdot 7H_2O$ | - 4.0 | $MgSO_4 \cdot 7H_2O$ | - 0.0 |
| $NaH_2PO_4 \cdot H_2O$ | - 0.0 | $NaH_2PO_4 \cdot H_2O$ | - 8.24 |
| $Na_2HPO_4$ | - 0.0 | $Na_2HPO_4$ | - 1.16 |
| NaCl | - 9.25 | NaCl | - 9.25 |
| CaCl | - 2.0 | $Na_2C_2O_4$ | - 0.80 |
| $Na_3C_6H_5O_7 \cdot 10 H_2O$ (sodium citrate) | - 0.8 | $Na_3C_6H_5O_7 \cdot 10 H_2O$ | - 0.80 |
| Natural Urine | - 10% volume of active stone-former's urine | Natural Urine | - 10% volume of active stone-former's urine |

The feed solutions were fed at equal rates to the CMSMPR at a rate of 12 ml/min, and after ten retention time cycles with a means retention time of ten minutes the samples were input to a Coulter Electronics Co. Model T Particle Counter. A plot of log $n$ vs. L was made for the resultant calcium oxalate dihydrate crystals and it was found that a substantially straight line could be drawn through the plot points, as shown in FIG. 2. From the slope and intercept of the best line, it was determined that G = 0.324 microns/min and $B^\circ$ = 35,000 nuclei/ml-min.

EXAMPLE II

The same feed solutions as in EXAMPLE I were formulated, except that natural urine from a normal non-stone-former was used. It was found, however, that spontaneous crystallization occurred in Feed 1. Accordingly, the experiment was repeated using 20% by volume of the non-stone-former's urine in Feed 2 and none in Feed 1 (yielding 10% of natural urine in the CMSMPR). The same proceduce was followed and it was found that G = 0.409 and $B^\circ$ = 12,000. Adding the urine aliquot to the calcium-loaded stream was found to advantageously deter spontaneous precipitation.

EXAMPLE III

The same feed solutions were run as blanks, i.e., no aliquot of natural urine was added to the feed. The same procedure was followed and it was found the G = 0.504 and $B^\circ$ = 2,000.

Examples I–III were repeated with fresh urine samples from the same donors and gave essentially the same experimental results.

EXAMPLE IV

Example I (stone-former) was repeated, but with twice the flowrate through the crystallizer (giving a mean retention time of 5 minutes) but with a 10% urine aliquot (total feed basis) from another stone-former and with the urine aliquot added to the calcium-loaded stream. The results were G = 0.93 and $B^\circ$ = 7,800.

EXAMPLE V

Example II (normal) was repeated with the changed conditions of Example IV with urine from a new non-stone-former with the results G = 0.73 and B = 4,600.

EXAMPLE VI

Example III (blank) was repeated with the high flow rate of Example IV with the results G = 0.83 and $B^\circ$ = 2,300.

It is observed that the level of growth and nucleation rates depend on the mean retention time in the system and a standard convenient value of retention time must be fixed when using these data comparatively. A value of about 10 minutes for the means retention time comprises such an acceptable level.

EXAMPLE VII

Example III (blank) was repeated, but with the addition of 50 mg/l of sodium pyrophospate, a known inhibitor. The results were $G = 0.44$ and $B^0 = 1,100$. It was thus observed that the present method is useful in screening possible drugs which are tested using an aliquot of a particular stone-former's urine.

We claim:

1. A method of determining crystallization properties of urine to study stone formation therein, comprising the steps of:
   formulating a first feed solution which includes synthetic urine plus an aliquot of natural urine;
   formulating a second feed solution which includes synthetic urine;
   combining said feed solutions in a continuous crystallizer; and
   measuring the crystal populations of the contents of the continuous crystallizer.

2. The method as defined by claim 1 wherein said synthetic urine comprises a plurality of salts dissolved in water to obtain the cations sodium, potassium, calcium, ammonium and magnesium, and the anions chloride, sulfate, oxalate and phosphate.

3. The method as defined by claim 1 wherein said second feed solution includes an aliquot of natural urine.

4. The method as defined by claim 3 wherein the percentage of natural urine in said first and second feed solutions is in the range of about three percent to thirty percent.

5. The method as defined by claim 1 wherein the percentage of natural urine in said feed solutin is in the range of about three percent to thirty percent.

6. The method as defined by claim 5 wherein said percentage is about twenty percent.

7. The method as defined by claim 1 further comprising the step of calculating the crystallization kinetics of said contents as a function of said crystal populations.

8. The method as defined by claim 7 wherein the two feed solutions respectively contain calcium and oxalate ions in amounts sufficient to cause supersaturation in the continuous crystallizer.

9. The method as defined by claim 7 wherein said second feed solution includes an aliquot of natural urine.

10. The method as defined by claim 9 wherein the percentage of natural urine in said first and second feed solutions is in the range of about 3 percent to 30 percent.

11. The method as defined by claim 10 wherein the two feed solutions respectively contain calcium and oxalate ions in amounts sufficient to cause supersaturation in the continuous crystallizer.

12. The method as defined by claim 9 wherein said percentage is about 10 percent.

13. The method as defined by claim 12 wherein said synthetic urine comprises a plurality of salts dissolved in water to obtain the cations sodium, potassium, calcium, ammonium and magnesium, and the anions chloride, sulfate, oxalate and phosphate.

14. The method as defined by claim 13 wherein the two feed solutions respectively contain calcium and oxalate ions in amounts sufficient to cause supersaturation in the continuous crystallizer.

15. Apparatus for determining the crystallization kinetics of urine to study stone formation therein, comprising:
    first and second feed means for carrying urine-containing solutions;
    a mixed suspension mixed product removal crystallizer chamber coupled to said first and second feed means;
    particle counting means adapted to receive samples of the output of said chamber; and
    computing means responsive to the output of said particle counting means for determining crystallization kinetics occurring in said chamber.

16. Apparatus as defined by claim 15 further comprising first and second continuous feed pumps respectively coupling said first and second feed means to said chamber.

17. Apparatus as defined by claim 15 wherein the volume of said chamber is of the order of 100 milliliters.

18. Apparatus as defined by claim 17 further comprising first and second continuous feed pumps respectively coupling said first and second feed means to said chamber.

19. A method of determining crystallization properties of urine to study stone formation therein, comprising the steps of:
    providing a continuous crystallizer unit;
    feeding to said continuous crystallizer unit a first feed solution which includes synthetic urine plus an aliquot of natural urine;
    feeding to said continuous crystallizer unit a second feed solution which includes synthetic urine;
    at least one of said feed solutions containing calcium ions and at least one of said feed solutions containing oxalate ions; and
    measuring the crystal populations of the contents of said continuous crystallizer unit.

20. The method as defined by claim 19 further comprising the step of calculating the crystallization kinetics of said contents as a function of said crystal populations.

* * * * *